(12) United States Patent
Geiger et al.

(10) Patent No.: US 10,058,692 B2
(45) Date of Patent: Aug. 28, 2018

(54) CONNECTOR FOR DIALYZER

(71) Applicant: B. BRAUN AVITUM AG, Melsungen (DE)

(72) Inventors: Ralph Geiger, Felsberg (DE); Christof Schlitt, Obergrenzebach (DE)

(73) Assignee: B. BRAUN AVITUM AG, Melsungen (DE)

( * ) Notice: Subject to any disclaimer, the term of this patent is extended or adjusted under 35 U.S.C. 154(b) by 169 days.

(21) Appl. No.: 15/019,014

(22) Filed: Feb. 9, 2016

(65) Prior Publication Data

US 2016/0243347 A1  Aug. 25, 2016

(30) Foreign Application Priority Data

Feb. 25, 2015 (DE) .................. 10 2015 102 719

(51) Int. Cl.
*B01D 11/00* (2006.01)
*B01D 61/00* (2006.01)
(Continued)

(52) U.S. Cl.
CPC .............. *A61M 39/10* (2013.01); *A61M 1/14* (2013.01); *A61M 1/367* (2013.01);
(Continued)

(58) Field of Classification Search
CPC ........... A61B 5/055; A61J 1/14; A61J 1/1475; A61M 1/14; A61M 1/16; A61M 1/168; A61M 1/1603; A61M 1/1605; A61M 1/1607; A61M 1/1609; A61M 1/1615; A61M 1/1619; A61M 1/1654; A61M 1/1656; A61M 1/342; A61M 1/3465; A61M 1/36; A61M 1/367; A61M 1/3609;
(Continued)

(56) References Cited

U.S. PATENT DOCUMENTS 4,745,950 A   5/1988   Mathieu
5,004,548 A * 4/1991   Richalley ............ A61M 1/3643
                                                    210/321.72
(Continued)

FOREIGN PATENT DOCUMENTS

DE       3513205      1/1987
DE       38 255 73    2/1990
(Continued)

OTHER PUBLICATIONS

German Search Report for DE 10 2015 102 719.4 dated Sep. 29, 2015, with translation.
(Continued)

Primary Examiner — Hayden Brewster
(74) Attorney, Agent, or Firm — RatnerPrestia

(57) ABSTRACT

A connector for connecting a dialyzer to a fluid-carrying line is disclosed, wherein the connector includes a coupling portion, especially a male Hansen connector portion, for fluid-tight connection to a connector element, especially a female Hansen connector adapter, of the line. In a flow channel of the connector, a shut-off device is integrated, which below a predetermined pressure or when no fluid communication is provided between the dialyzer and the line shuts off the flow cross-section of the flow channel.

13 Claims, 10 Drawing Sheets

(51) Int. Cl.
*A61M 39/10* (2006.01)
*A61M 1/14* (2006.01)
*A61M 39/20* (2006.01)
*A61M 39/24* (2006.01)
*A61M 1/36* (2006.01)
A61M 39/26 (2006.01)

(52) U.S. Cl.
CPC .......... *A61M 1/3644* (2014.02); *A61M 39/20* (2013.01); *A61M 39/24* (2013.01); *A61M 1/3643* (2013.01); *A61M 39/26* (2013.01); A61M 2039/1027 (2013.01); A61M 2039/1072 (2013.01); A61M 2039/1077 (2013.01); A61M 2039/242 (2013.01); A61M 2039/244 (2013.01)

(58) Field of Classification Search
CPC .............. A61M 1/3626; A61M 1/3643; A61M 1/3644; A61M 1/3646; A61M 1/3649; A61M 39/10; A61M 39/20; A61M 39/24; A61M 39/26; A61M 29/10; A61M 39/16; A61M 2001/165; A61M 2001/3437; A61M 2039/1027; A61M 2039/1072; A61M 2039/1077; A61M 2039/1088; A61M 2039/167; A61M 2039/242; A61M 2039/244; A61M 2202/0413; A61M 2205/12; A61M 2205/331; A61M 2205/3306; A61M 2205/75; A61M 2230/20; B01D 17/12; B01D 21/30; B01D 21/302; B01D 21/34; B01D 35/00; B01D 35/143; B01D 35/1435; B01D 35/147; B01D 35/153; B01D 61/12; B01D 61/22; B01D 61/32; C02F 1/003; C02F 1/008; C02F 1/325; C02F 2209/00; C02F 2209/001; C02F 2209/003; C02F 2209/04; C02F 2209/05; C02F 2209/055; C02F 2209/06; C02F 2209/07; C02F 2209/08; C02F 2209/09; C02F 2209/10; C02F 2209/11; F24H 1/00; F16K 49/002
USPC ...................................................... 137/798
See application file for complete search history.

(56) References Cited

U.S. PATENT DOCUMENTS

| | | | |
|---|---|---|---|
| 5,015,374 | A | 5/1991 | Mathieu et al. |
| 5,167,398 | A | 12/1992 | Wade et al. |
| 5,294,092 | A | 3/1994 | Wade |
| 5,534,228 | A * | 7/1996 | Wesseler ............... A61M 39/10 |
| | | | 422/541 |
| 6,858,137 | B2 | 2/2005 | Hahmann et al. |
| 2004/0068238 | A1 | 4/2004 | Utterberg et al. |
| 2004/0199143 | A1* | 10/2004 | Lauer .................... A61M 39/14 |
| | | | 604/533 |
| 2009/0004053 | A1 | 1/2009 | Kenley |
| 2011/0306940 | A1 | 12/2011 | Miyasaka |
| 2016/0129174 | A1 | 5/2016 | Hundertmark |

FOREIGN PATENT DOCUMENTS

| | | |
|---|---|---|
| DE | 4203417 | 8/1992 |
| DE | 102014100326 | 10/2014 |
| EP | 1 000 632 | 5/2000 |
| WO | WO 2005/046785 | 5/2005 |
| WO | 2006122406 | 11/2006 |
| WO | WO 2009/063281 | 5/2009 |

OTHER PUBLICATIONS

European Search Report dated Oct. 14, 2016 for European Application No. 16155908.3, including English translation, 13 pages.

* cited by examiner

CONNECTOR FOR DIALYZER

CROSS REFERENCE TO RELATED APPLICATIONS

This application claims priority to German Application No. DE 10 2015 102 719.4 filed Feb. 25, 2015, the contents of such application being incorporated by reference herein.

FIELD OF THE INVENTION

The invention relates to a connector unit for connecting a junction port of a dialyzer comprising a fluid-carrying line, wherein the connector unit includes a continuous flow channel and on one side of the flow channel includes a coupling portion for fluid-tight connection to the junction port of the dialyzer and on the other side of the flow channel includes a coupling portion for fluid-tight connection to the fluid-carrying line. Moreover it relates to a method of flushing a filter element, especially a dialyzer for extracorporeal blood treatment methods, such as for dialysis, hemofiltration or ultrafiltration, using said connector unit.

BACKGROUND OF THE INVENTION

Known dialyzers usually include four ports by which they are connected, on the one hand, to a line system of a dialysis machine and, on the other hand, to an extracorporeal blood system connected to a patient. Said ports are split into two ports for connection to the extracorporeal blood system via which blood to be purified is supplied to the dialyzer and drained from the dialyzer hereinafter also referred to as blood ports, and two ports for connection to the dialysis machine via which the dialysis fluid is supplied to the dialyzer and drained from the dialyzer, hereinafter also referred to as dialysis fluid ports (see schematic of FIG. 1).

Before the start of a blood treatment method it is necessary to fill and flush the extracorporeal blood circuit including the dialyzer filter so as to remove the air present in the extracorporeal circuit and possible residues in the dialyzer. As a rule, flushing is performed with a common saline solution. For this purpose, a pre-filled bag including common saline solution is used which is manually connected to the arterial blood hose end. The blood pump of the dialysis machine then conveys the fluid through the extracorporeal circuit. The common saline solution finally exits the venous end of the blood hose into a waste bag. After circulating sufficient fluid the extracorporeal circuit is flushed and filled and thus prepared for the blood treatment.

In order to prevent impurities from penetrating the dialyzer and fluid possibly present in the same from leaking as well as to protect the ports from damage the ports of the dialyzer are initially covered and closed.

For the afore-described flushing operation the caps closing the blood ports of the dialyzer have to be removed. They are then usually attached to the dialysis fluid ports. After flushing, the caps are removed from the dialysis fluid ports so that the feed and respective drain lines of the dialysis fluid hose system can be attached thereto.

DESCRIPTION OF THE RELATED ART

There are solutions in which all four ports of a dialyzer are closed by separate caps. For example, from DE 38 255 73 A1 a sealing cap for dialyzers is known for use to sterilize the same comprising first and second cap parts the first cap part of which can be attached to a dialysis flange. The second cap part is movable between an open position in which a sterilizing medium passes through and a closed position. The first cap part includes an outer sleeve outwardly encompassing the dialyzer flange in the mounted condition in a sterile sealing manner and a rear part which is adapted to be fluid-communicated with an in-line sterilizing device.

From EP 1 000 632 A2 moreover a closure element for the sterile sealing of ports of filter modules for dialysis, hemofiltration or ultrafiltration (a sterile barrier as it is called) is known comprising a wall which includes an automatically closing slit-like cut which seals off germproof in the closed state. There are provided fastening means which are adjacent to the wall and with which the sealing element can be connected to a port.

From US 2009/0004053 A1 a system is known by which a medical apparatus can be automatically purified, disinfected, tested and activated. The system comprises a dialyzer including a blood inlet and a blood outlet, a blood outlet line for connection to the blood outlet having a machine-side end and a patient-side end, a blood inlet line for connection to a blood inlet having a machine-side end and a patient-side end, an adaptor for connection to the dialyzer and a re-using means for pairing with the dialyzer. The adaptor comprises plural connectors designed for connection to the patient-side ends of the blood inlet and blood outlet lines. The re-using means is designed for pairing with the adapter and is arranged for purifying the blood inlet line, the blood outlet line and the dialyzer.

From WO 2009/063281 A1 a medical connector for connecting a dialysate supply line or a dialysate drain line to a fluid port of a dialysis machine is known. The connector has a visible signal device made of a color strip arranged on a journal. The signal is visible when the journal is provided in a correctly engaged position with an external element. Otherwise the portion of the journal bearing the signal is lowered so that the signal is not visible and indicates an incorrect connection. The fluid port of the dialysis machine is provided with a stop valve.

From WO 2005/046785 A1 a connector for connecting a dialysate port of a blood dialyzer to a line carrying a dialysate is known. The connector includes a cavity passing through the same, a first end enclosing the cavity which is suited for accommodating the dialysate port in the cavity and a second end enclosing the cavity which is suited for being connected to the dialysate-carrying line. At the first end a recess including a slide element received by the recess is provided. The slide element is movable between first and second positions perpendicularly to the direction of the cavity in the first end. In the first position the slide element does not penetrate the cavity of the first end and in the second position constricts the cavity of the first end so that the connector with the slide element in the first position is attached to the dialysate port and in the second position can be locked to the dialysate port by an undercut provided on the latter.

SUMMARY OF THE INVENTION

The use of caps for sealing dialysis fluid ports of a dialyzer known from the state of the art entails plural drawbacks:

During the afore-described change of the caps for flushing the dialyzer, contamination, deformations or a loss of the caps may disadvantageously occur. Furthermore, the case may arise that the caps are not correctly closed again. If the user happens to drop a cap during the change, said cap is contaminated and cannot be used any more. If it is nevertheless erroneously used, the cap may contaminate the port and thus the dialysis fluid and hence the filter cannot be used any longer. In such case the use of the dialysis filter is no longer possible.

Finally after flushing the dialyzer with a washing solution the cap has to be removed, when dialysis fluid lines are connected to the dialysis fluid ports of the dialyzer. In this case, as a rule washing solution still provided in the dialyzer is leaking. It was observed that users partially close the dialysis fluid ports temporarily by a finger, for example, in order to minimize or prevent such leakage. This results disadvantageously in a further possibility of contamination.

Another drawback consists in the fact that the time of removing the caps is different and is handled differently from user to user. In this way the ports (both blood ports and dialysis fluid ports) may be provided to be open, i.e. unprotected, on the machine.

Starting from the afore-described state of the art, the present invention is based on the object to eliminate the afore-listed drawbacks, and especially to provide a system in which fluid can be prevented from leaking in fluid lines which are not connected to the dialyzer, for example when connecting the dialyzer, especially washing liquid after flushing the dialyzer. Preferably the system is intended to be adapted to existing medical apparatuses and hence to prevent fluid from leaking in the case of an uncoupled dialyzer also in known dialyzers and connection systems. Moreover, it is to be ensured that even when the dialyzer is uncoupled it is sealed in a sterile manner.

The object is achieved by the features of the independent claims. Advantageous developments are the subject matter of subclaims.

In accordance with the invention, a connector for connecting a port of a dialyzer to a fluid-carrying line is provided. The fluid-carrying line may be a blood supply line, a blood drain line, a dialysis fluid supply line and a dialysis fluid drain line. The connector has a coupling portion, especially a male Hansen connector portion, for fluid-tight connection to a connecting element, especially a female Hansen connector adapter, of the corresponding line. In a flow channel of the connector a shut-off device or flow resistor is integrated which shuts off the flow cross-section of the flow channel in a fluid-tight manner below a predetermined pressure and/or when no (fluid) connection is present between the port and the line, i.e. when the line is not connected to the connector, and which releases the flow cross-section of the flow channel, i.e. admits a fluid flow between the dialyzer port and the line, when a connection is present between the port and the line, i.e. when the line is connected to the connector and/or a fluid flow having a predetermined or higher pressure is built up.

This means that the connector seals the flow channel, when no line is connected and, respectively, no line has been connected so far. The flow channel is initially closed. Hence the dialyzer need not be closed by an additional closure or cap. Thus also a possible risk of contamination via the cap is omitted. Furthermore, in this way the port is prevented from being open and thus unprotected, even for a short time, between removing the cap and connecting the washing solution line. The dialyzer thus can be delivered and distributed, respectively, without any caps but still in a fluid-tight version. After flushing it can be ensured that the washing solution provided in the dialyzer does not leak before the dialysis fluid drain and supply lines are connected.

At the connectors of the dialysis fluid supply line and the dialysis fluid drain line, which remain open during the flushing operation, the limit pressure from which the respective shut-off device opens may be appropriately preset or settable so that said pressure is higher than the fluid pressure to be expected during the flushing operation on the dialysis fluid side of the dialyzer.

The connector may take the shape of an adapter or a connector unit, i.e. of a separate component, adapted to be mounted to the connecting port of the dialyzer or may be part of the connecting port of the dialyzer itself and, respectively, may be integrally formed with the same.

The invention provides a connection system for connecting fluid-carrying lines to appropriate ports of a dialyzer, wherein the connecting system itself includes means preventing fluid from leaking, if there is no tight fluid connection between the dialyzer and the fluid-carrying line. In the case of a separate connector unit, this unit may be used, depending on the configuration of its coupling portions on both sides, with any dialyzers and fluid lines, irrespective of the configuration of the respective provided ports.

In accordance with the invention, the connector unit is coupled to a port of a dialyzer or, respectively, is coupled thereto by a user. As soon as the connector unit and the dialyzer are coupled to each other, a flow communication exists between the corresponding port of the dialyzer and the flow channel of the connector unit. Said communication is blocked with the shut-off device present in the flow channel according to aspects of the invention, unless a fluid line is coupled, especially in a fluid-tight manner, to the connector unit on the side opposite to the dialyzer. The flow channel in the connector unit is continuously formed by the connector unit and, in other words, leads from a connector input side to a connector output side. Depending on the flow direction of the connector unit, the connector input side or the connector output side may be arranged to be connected to the port of the dialyzer in a fluid-tight manner, and the connector output side and the connector input side may be arranged to be connected to the fluid-carrying line in a fluid-tight manner.

The flow resistance or, respectively, the shut-off device is designed so that the flow channel is released in the connector or in the connector unit as soon as a line is connected to the dialyzer and fluid is pumped through the dialyzer. In this way, the invention offers a system by which any dialyzer can be sealed in an especially simple and efficient manner, unless it is not connected to a line, wherein the sealing moreover can be released in an especially simple way by establishing a flow communication between the dialyzer and the fluid-carrying line. This is advantageously independent of the respective dialyzer. The system according to aspects of the invention can be used and employed both with dialyzers in which all ports or part of the ports are already provided with a port system selectively blocking the same and with dialyzers in which no port is provided with such selective sealing. Thus the connector unit according to aspects of the invention can be employed by a user of the dialyzer in an extremely flexible manner.

For example, at least one blood port or both blood ports of a dialyzer is/are coupled to a respective connector unit according to aspects of the invention and, respectively, the ports thereof are appropriately configured. Preferably one dialysis fluid port or both dialysis fluid ports of the dialyzer is/are additionally or alternatively also coupled to a respective connector unit according to aspects of the invention. In a flushing operation or priming operation usually to be performed prior to treatment, fluid lines now can be coupled or uncoupled in any way to/from the line-side coupling portion of the respective connector unit without fluid leaking from the dialyzer when the line is uncoupled. The use of caps known from the state of the art and described in the beginning for closing the dialyzer ports thus is superfluous.

The invention can in total entail definite increase in the safety of an extracorporeal blood treatment to prevent infection of the patient by contamination. Furthermore, facilitated handling can be brought about for the user, linked with a lower possibility of contamination. Finally misuse can be avoided. Ultimately cost savings can be caused as the caps known from and required in prior art can be dispensed with. However, it is a particular advantage that the connector system according to aspects of the invention may constitute an additional sterile barrier depending on the design. Especially an additional oxygen exclusion from the dialyzer filter may be obtained.

Advantageous embodiments of the invention are claimed, inter alia, in the subclaims and will be hereinafter illustrated in detail.

A dialyzer in accordance with the present description of the invention is understood to be especially a filter module for the extracorporeal blood treatment. A fluid-carrying line in accordance with the present description of the invention is understood to be especially a fluid supply line or fluid drain line, especially a fluid supply line or fluid drain line of an apparatus for extracorporeal blood treatment such as a dialysis machine.

At least one of the coupling portions of the connector unit may be a quick-action coupling portion, for example a Hansen coupling element. Preferably a coupling portion of the connector unit includes a female connector adapter, in particular a female Hansen connector adapter. The latter is formed and suited for connection to a female counter element, especially a male Hansen connector element. Especially the port-side coupling portion of the connector may be configured to have such female connector adapter, especially a female Hansen connector adapter, so that the connector unit has to be connected to a connecting port of the dialyzer of a Hansen coupling type frequently designed as male counter element, especially as male Hansen connector counter element. Such connection can be made and released advantageously in an especially simple manner by a user and is wide-spread in the field of extracorporeal blood treatment apparatuses so that high compatibility of the connector unit according to aspects of the invention can be assumed.

According to one embodiment of the invention, the connector unit includes two connector elements adapted to be coupled to and uncoupled from each other. Especially the one connector element may have a male coupling portion for mutual coupling to the other connector element and the other connector element may have a female coupling portion for mutual coupling to the one connector element. In this way, the two connector elements of the connector unit are adapted to be coupled to and uncoupled from each other in an especially simple and user-friendly manner. In at least one of the connector elements, preferably in the dialyzer-side connector element, a shut-off device according to aspects of the invention is arranged. Such configuration of the connector unit offers special advantages in case when a dialyzer is used the ports of which have no sterile barriers or similar units blocking the ports of the dialyzer. The connector unit is coupled to a port of the dialyzer in the afore-described manner. In the case of a flushing operation or a priming procedure the port-side connector element remains coupled to the connecting port of the dialyzer, while the fluid line is separated therefrom by uncoupling the two connector elements from each other. As a result, also in a dialyzer not being provided with blocking means a change of fluid lines, for example from the blood ports to the dialysis fluid ports and vice versa, can be carried out without fluid being allowed to leak from the dialyzer or the ports thereof being open and possibly contaminated with the fluid lines being released. It can also be stated that one of the connector elements acts as a type of adapter which a user can detachably connect to the connector.

The respective coupling portions of the connector unit and, respectively, of the connector elements can be formed especially as male Hansen coupling element and female Hansen coupling element. According to one embodiment, each of the two connector elements includes a female coupling portion and a male coupling portion.

According to one embodiment of the invention, the shut-off device can be opened in a pressure-dependent and direction-independent manner. In this way, the shut-off device can be opened independently of the respective port configuration and the contingent flow direction. In the case of uncoupled fluid lines the pressure difference prevailing at the shut-off device is so small or not present that the shut-off device shuts off the flow channel and no fluid can pass and thus leak. When the fluid line is coupled, a pressure difference sufficient for opening the shut-off device is prevailing at the latter, namely irrespective of whether the respective port is an inlet or an outlet. This solution is very user-friendly.

According to another embodiment of the invention, the shut-off device comprises a check valve. Hence the connector unit and, respectively, the connector can be specifically formed to have only one flow direction, which contributes to avoiding misuse. In order to permit both flow directions the shut-off device may also be in the form of a bidirectional check valve.

In accordance with an aspect of the invention, the shut-off device can be opened during connection of the line to the connector with an actuator provided at a connector element of the line to be connected. For example, the actuator can bring or displace the shut-off device into an opened position.

It is of particular advantage when the shut-off device comprises a membrane blocking the flow cross-section, especially a hydrophobic membrane. It can be permeable to air. The membrane may be formed so that it opens, for example tears or bursts, at a particular pressure difference prevailing at the same, or that it opens only by being punctured by a dedicated puncturing element. Preferably the membrane is configured so that it closes again automatically when the fluid line is disconnected, for example in the way of an access port generally known in medical engineering.

The shut-off device is preferably configured in all embodiments such that it can be repeatedly used, i.e. that it is open when the fluid line is coupled and shuts off when the fluid line is uncoupled, which is preferably largely independent of the number of already performed coupling operations.

In one embodiment the connector unit may include an opening element for opening the shut-off device. The opening element is preferably arranged in one of the two connector elements. It is configured to necessarily puncture and open the shut-off device upon coupling the fluid line to the dialyzer. The opening element is preferably a puncturing element. Preferably the female connector element is formed to activate the shut-off device.

In other words, the invention relates to the integration of a shut-off device in a connector system, for example by a connector having at least one of the following characteristics:

The connector renders it obsolete to use caps and to keep closed and seal disconnected ports by the thumb.

The connector may consist of check valves and may be compatible with all apparatus manufacturers.

The connector can be activated by a female Hansen connector. The invention includes a connector to a male connector and an activator to a female Hansen connector (female Hansen connector remains compatible with other male connectors).

The connector can open in a pressure-dependent and direction-independent manner.

The shut-off function can be performed by mounting a membrane. The membrane can have a hydrophobic structure and thus can be permeable to air and can be punctured by connecting an appropriately formed second connector.

In the aforementioned embodiments the connector can always be statically connected to the dialyzer and includes a shut-off device. The user need not take any additional manual handling steps.

The invention further relates to a method of flushing a dialyzer for an extracorporeal blood treatment, the dialyzer comprising a blood supply line port, a blood drain line port, a dialysis fluid supply line port and a dialysis fluid drain line port, wherein a connector according to any one of the preceding claims is arranged on at least one port of the dialyzer, preferably on each port of the dialyzer, and the dialyzer is flushed by coupling a washing fluid supply line to the connector arranged at the blood supply line port and a washing fluid drain line is coupled to the connector arranged at the blood drain line port.

The method according to aspects of the invention ensures that upon uncoupling or releasing one of the fluid lines the connector unit according to aspects of the invention or at least the connector element including the shut-off device always remains coupled to the corresponding port of the dialyzer and in this way prevents fluid from leaking therefrom. In other words, fluid, especially washing solution during initial flushing, is prevented from leaking by a shut-off device statically connected to the dialyzer. The user does not have to actively take any further handling steps for this purpose. This entails increased safety, facilitated applicability and less contamination.

BRIEF DESCRIPTION OF THE DRAWINGS

The invention is best understood from the following detailed description when read in connection with the accompanying drawings. Included in the drawings are the following figures.

DETAILED DESCRIPTION OF THE FIGURES

Figure 1:
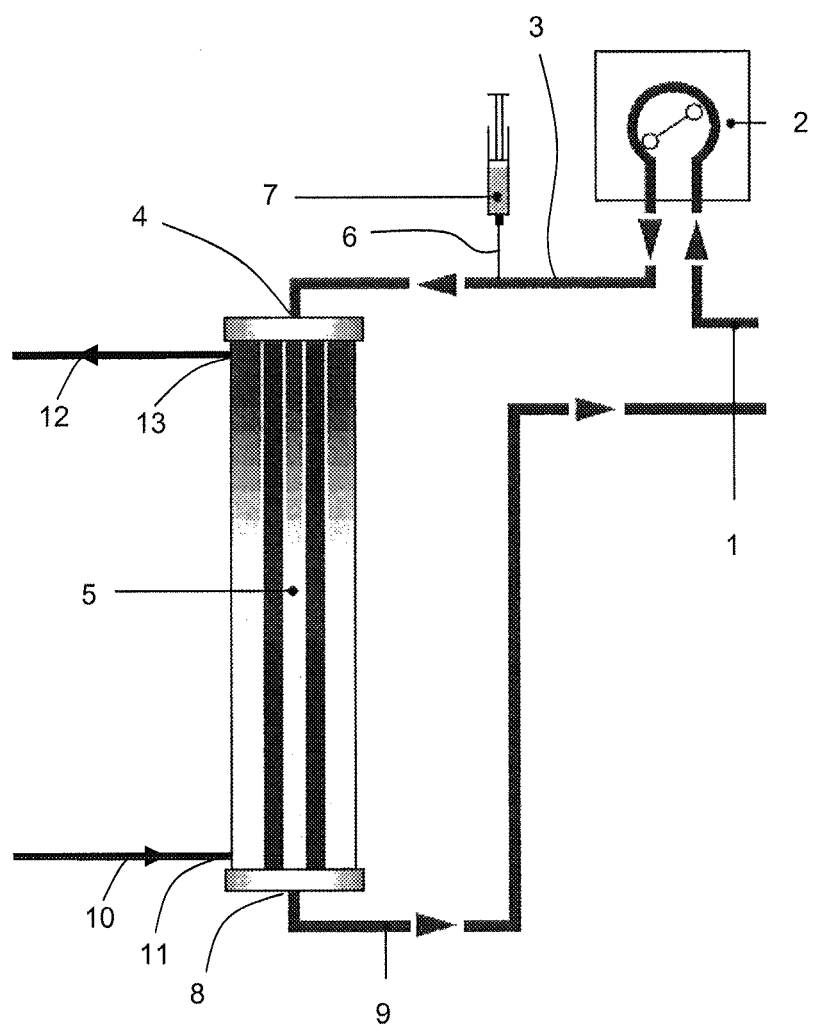
FIG. 1 shows a schematic of a fluid system of an apparatus for extracorporeal blood treatment.

FIG. 1 exemplifies a cutout of an apparatus for extracorporeal blood treatment, in this case a dialysis apparatus. There is substantially shown the entire extracorporeal blood circuit of the apparatus. It comprises an arterial blood line 1 with which blood is guided from a patient (not shown) to a peristaltic pump 2 of the treatment apparatus. On the high-pressure side of the peristaltic pump 2 a high-pressure blood line or blood supply line 3 supplies blood being under high pressure but still untreated to a blood supply line port 4 of a dialyzer 5. Downstream of the peristaltic pump 2, additives, e.g. anticoagulants or heparin for hemodilution, may be added to the blood provided in the system with a supply line 6 and a pump 7. In the dialyzer 5 blood is treated, e.g. purified, in a known way by the dialysis fluid. Treated blood is fed via a blood drain port 8 from the dialyzer 5 via a venous blood line or blood drain line 9 back to the patient.

Fresh dialysis fluid is supplied to the dialyzer 5 via a dialysis fluid supply line 10 coupled to a dialysis fluid supply line port 11 of the dialyzer 5. Used dialysis fluid is removed via a dialysis fluid drain line 12 coupled to a dialysis fluid drain line port 13 of the dialyzer 5 from the latter and is supplied to disposal or recycling (not shown). FIG. 1 illustrates that in the reverse flow blood and dialysis fluid flow through the dialyzer 5.

Before the start of treatment the dialyzer 5 is flushed with a washing solution through the blood ports 4 and 8. For this purpose, usually a bag pre-filled with saline solution is manually connected to the arterial blood hose end and said saline solution is pumped through the extracorporeal circuit including the dialyzer 5 with the peristaltic pump 2. The saline solution finally exits at the venous end of the blood hose 9, e.g. into a waste bag. After sufficiently circulated fluid the extracorporeal circuit is flushed and filled and thus prepared for the blood treatment.

Figure 2:
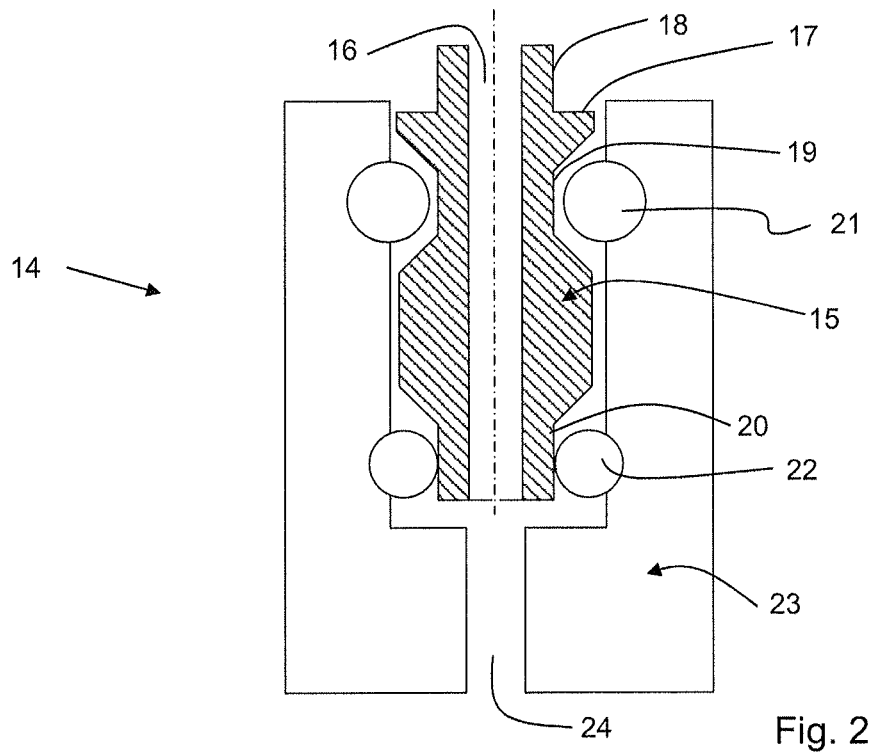
FIG. 2 shows a schematic of a dialyzer connection known from the state of the art.

FIG. 2 illustrates by way of example and schematically a prior art connector 14 which includes a connecting element 15 forming a connection or port of the dialyzer 5 in the form of a male Hansen connector element. This is a hollow cylinder-type element known per se having a continuous flow channel 16. On the side close to the dialyzer the connecting element 15 is provided with a pin 18 delimited by a shoulder 17 which serves for a permanent arrangement of the connecting element 15 at the dialyzer 5. On the side of the shoulder 17 facing away from the pin 18 a circumferential annular groove 19 is introduced into the outer contour of the connecting element 15. On the line side a stepped end-side offset 20 is introduced into the outer contour of the connecting element 15. The groove 19 and the offset 20 serve for receiving coupling elements in the form of balls 21, 22 which are received in a female Hansen connector element 23 to be movable in the radial direction and radially inwardly biased but fixed in the axial direction. In said female Hansen connector element a continuous flow channel 24 is formed. The female Hansen connector element 23 is tightly connected to one of the fluid lines 3, 9, 10, 12 on the side opposite to the male connecting element 15. It is obviously evident from FIG. 2 that, when disconnecting the fluid line 3, 9, 10, 12 from the dialyzer by uncoupling the female Hansen connector element 23 from the connecting element 15, the flow channel 16 thereof is and remains open so that in a disadvantageous manner fluid can flow out of the interior of the dialyzer 5 and moreover impurities may penetrate the interior of the dialyzer 5 and contaminate the latter.

FIGS. 3 to 12 illustrate different embodiments of the invention, wherein in the shown examples a Hansen connector is always used as a coupling principle. It has been described in the foregoing already with reference to the state of the art and is generally known so that further description in this respect will be renounced in the following examples and the foregoing remarks will be referred to. It is noted that the invention can also be used together with other coupling systems and connections and is not restricted to the use of a Hansen connector. Furthermore, instead of a male Hansen connector element a female Hansen connector element may be provided and vice versa.

Figure 3:
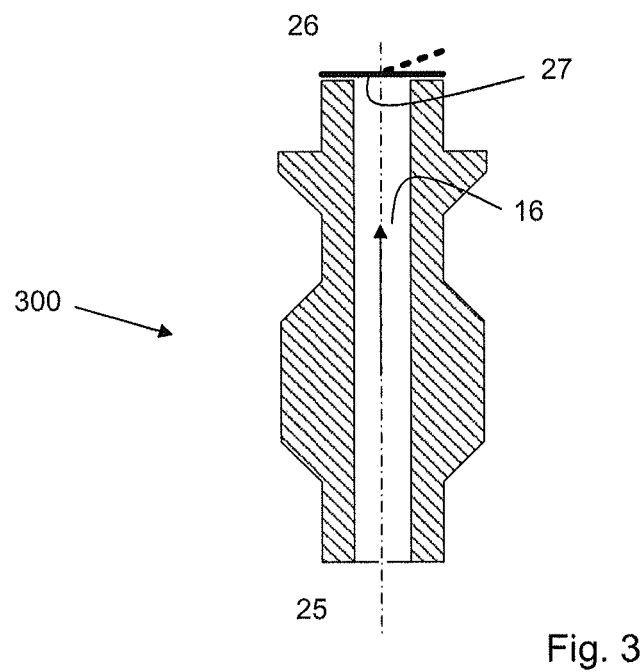
FIG. 3 shows a schematic of a first embodiment of the invention in a sectional view.

FIG. 3 shows a connector 300 in the form of a male Hansen connector 300 which, similarly to FIG. 2, is part of an input side connection or port 4, 11 (not shown) of the dialyzer 5 via which blood, washing solution or dialysis fluid is supplied to the dialyzer. The flow direction is appropriately marked by an arrow in FIG. 3. On the side 25 facing away from the dialyzer 5 (at the bottom in FIG. 3) a female connecting piece 23 can be pushed onto and coupled to the connector 300 from the line side 25. The flow channel 16 of the connector 300 is closed at the end 26 of the connector 300 facing the dialyzer 5 by a shut-off device in the form of a check valve 27 which is arranged or formed on the downstream side 25 or dialyzer side of the connector 300. The check valve 27 shuts off in the discharge direction, i.e. out of the dialyzer 5, and releases the flow channel 16 in the inflow direction, i.e. into the dialyzer 5. The check valve 27 shuts off in a fluid-tight manner as long as a pressure difference prevailing on the same is smaller than a predetermined limit value. When the limit value is exceeded, the check valve 27 opens and releases the flow channel 16. The check valve 27 is adjusted and biased, respectively, so that it opens as late as during operation of the pump 2 and by the pump pressure to be expected.

Figure 4:
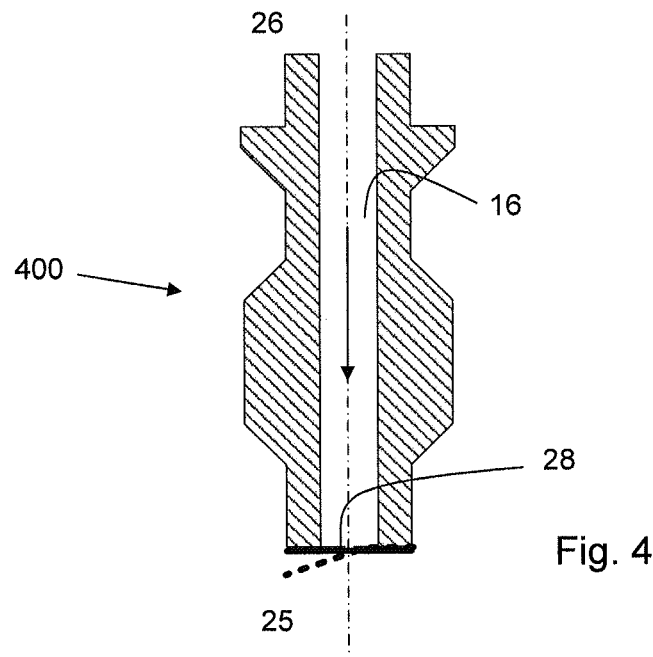
FIG. 4 shows a schematic of a second embodiment of the invention in a sectional view.

FIG. 4 illustrates a connector 400 resembling the connector 300 of FIG. 3 in the form of a male Hansen connector 400 which, similarly to FIG. 2, is part of an output side connection or port 8, 13 (not shown) of the dialyzer 5 through which blood or washing solution or dialysis fluid is discharged from the dialyzer 5. The flow direction is appropriately marked by an arrow in FIG. 4 and is opposed to the flow direction in FIG. 3. On the side facing away from the dialyzer 5 (at the bottom in FIG. 3) a female connecting piece 8, 13 can be pushed from the fluid line side 25 onto and can be coupled to the connector 400. The flow channel 16 of the connector 400 is closed by a shut-off device in the form of a check valve 28 arranged and formed on the downstream side or fluid line side 25 of the connector 400. The check valve 28 shuts off in the inflow direction, i.e. into the dialyzer 5, and releases the flow channel 16 in the discharge direction, i.e. out of the dialyzer 5, wherein the check valve 28 does not automatically open to the outside but only with an appropriate pump pressure so that without any pump operation it seals the connecting port 8 and, respectively, 13 in a fluid-tight manner.

Figure 5:
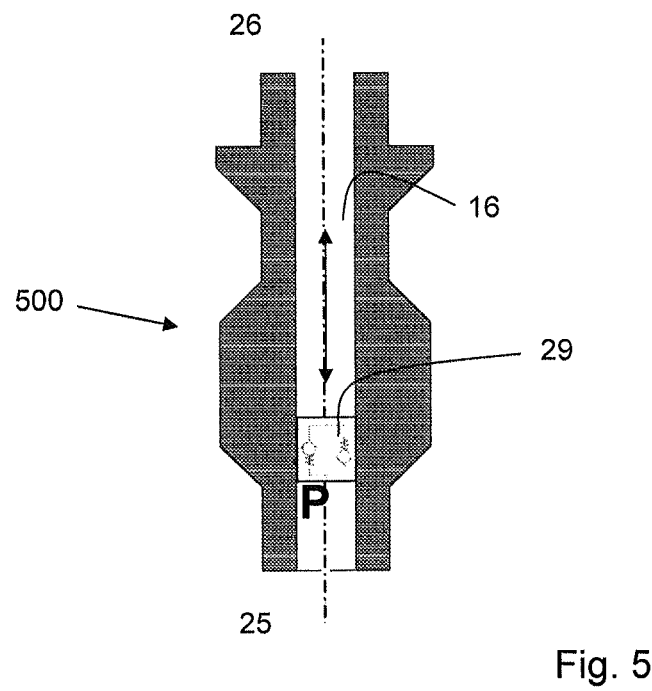
FIG. 5 shows a schematic of a third embodiment of the invention in a sectional view.

FIG. 5 shows a connector 500 substantially representing a combination of the two embodiments shown in FIGS. 3 and 4. Instead of a check valve 27 opening to the inside with appropriate pressure or a check valve 28 opening to the outside with appropriate pressure, in the flow channel 16 a bidirectional check valve or valve system 29, respectively, is provided which operates in a pressure-dependent and direction-independent way. The valve system 29 shuts off both in the discharge direction and in the inflow direction as long as a pressure difference prevailing at the same is smaller than a predetermined limit value. When the limit value is exceeded, the valve system 29 opens and releases the flow channel 16 in the direction of the pressure difference, i.e. from the high-pressure side in the direction of the low-pressure side. In other words, the connector 500 is suitable independently of whether it is provided at an inlet or an outlet of the dialyzer 5. Again a female connecting piece 4, 8, 11, 13 can be pushed onto and coupled to the fluid line side 25.

Figure 6:
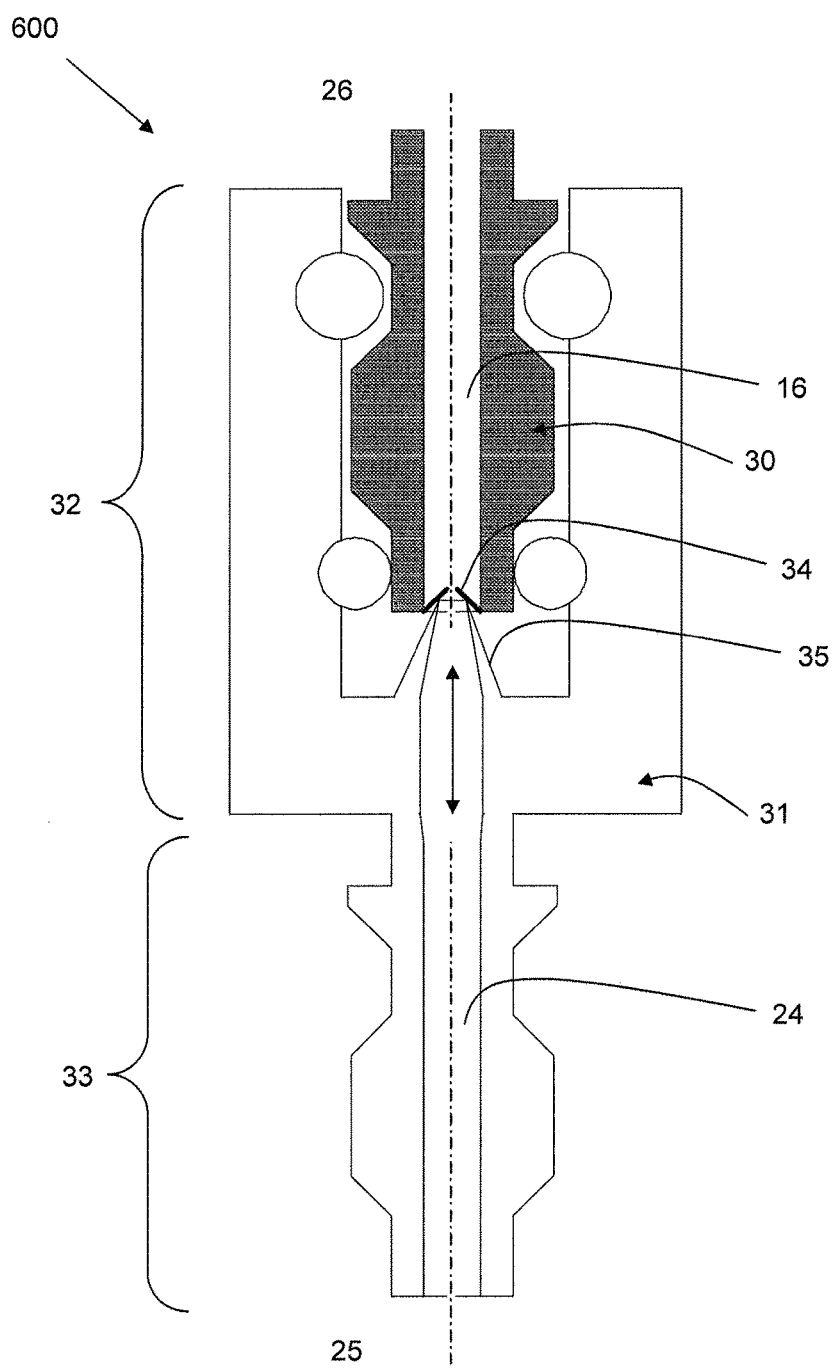
FIG. 6 shows a schematic of a fourth embodiment of the invention in a sectional view.

FIG. 6 shows a connector 600. It includes a male connector element 30 in the form of a male Hansen connector which, similarly to FIG. 2, is part of an input or output side connection or port 4, 8, 11, 13 (not shown) of the dialyzer 5 and includes a connector element 31 having a female coupling portion 32 and a male coupling portion 33, both of a Hansen type connector. The male coupling portion 33 of the connector element 31 is adapted to be coupled to a female Hansen connector element 23 (not shown in FIG. 5) of one of the lines 3, 9, 10, 12. The flow direction is marked again in FIG. 6, wherein the connector 600 may be provided both at an input side port 4, 11 and at an output side port 8, 13 with appropriately reverse flow direction and is suited for this purpose, respectively. In the connector element 30 a flow channel 16 is formed and in the connector element 31 a flow channel 24 is formed.

On its input side 25 (line side 25) the connector element 30 is closed by a shut-off device in the form of an especially mechanically operable or movable closing element 34. The closing element is arranged or formed on the side of the connector element 30 facing the connector element 31. The closing element 34 is automatically closed and thus, in the case of disconnection, shuts off the flow channel 16 in both directions in a fluid-tight manner. It releases the flow channel 16 in both directions as soon as a connection is brought about by intended coupling of the connector element 30 and the connector element 31. This is effectuated by an opening element 35 formed at the connector element 31 in that it urges the closing element 34 into an opened position or actuates the same in the case of intended connection. The opening element is a projection facing the connector element 30 which penetrates the flow channel 16 of the connector element 30 and there actuates or activates the closing element 34 provided there or a similar shut-off device so that it releases the flow channel 16 for both flow directions. A female connecting piece 4, 8, 11, 13 of the dialyzer 5 can be pushed onto and coupled to the coupling portion 33 of the connector element 31 from the fluid line side 25.

Figure 7:
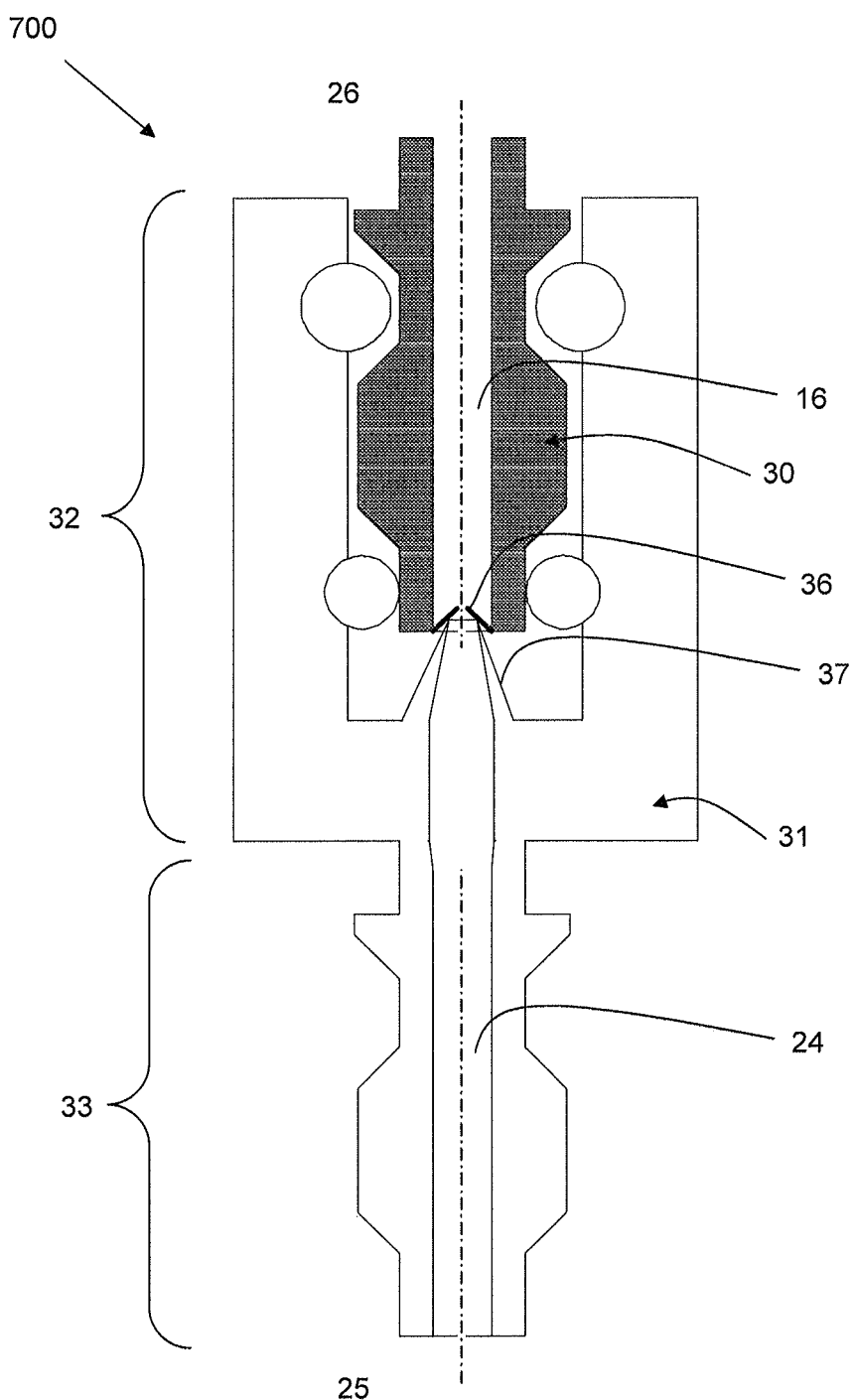
FIG. 7 shows a schematic of a fifth embodiment of the invention in a sectional view.

FIG. 7 illustrates a connector 700 which is similar to the connector 600 of FIG. 6 but differs by the fact that the flow channel 16 of the connector element 30 is not closed by the port 34 but by a shut-off device in the form of a hydrophobic membrane 36 which is arranged or formed on the fluid line side 25 and, respectively, on the side of the connector element 30 facing the connector element 31. The membrane 36 is automatically closed and thus shuts off the flow channel 16 in the case of disconnection both in the discharge direction and in the inflow direction. It releases the flow channel 16 in both directions as soon as a connection is brought about by intended coupling of the connector element 30 and the connector element 31. This is effectuated by an opening element 37 in the form of a puncturing needle formed at the connector element 31 in that the same punctures and opens the membrane 36 in the case of intended connection. When the connector elements 30 and 31 are uncoupled, the hydrophobic membrane 36 automatically closes in a fluid-tight manner.

Each of the FIGS. 8 to 12 shows a connector unit 800, 900, 1000, 1100 and 1200, each substantially corresponding to the connector unit 600 of FIG. 6 as well as to the connector unit 700 of FIG. 7 so that reference is made to the respective descriptions.

Figure 8:
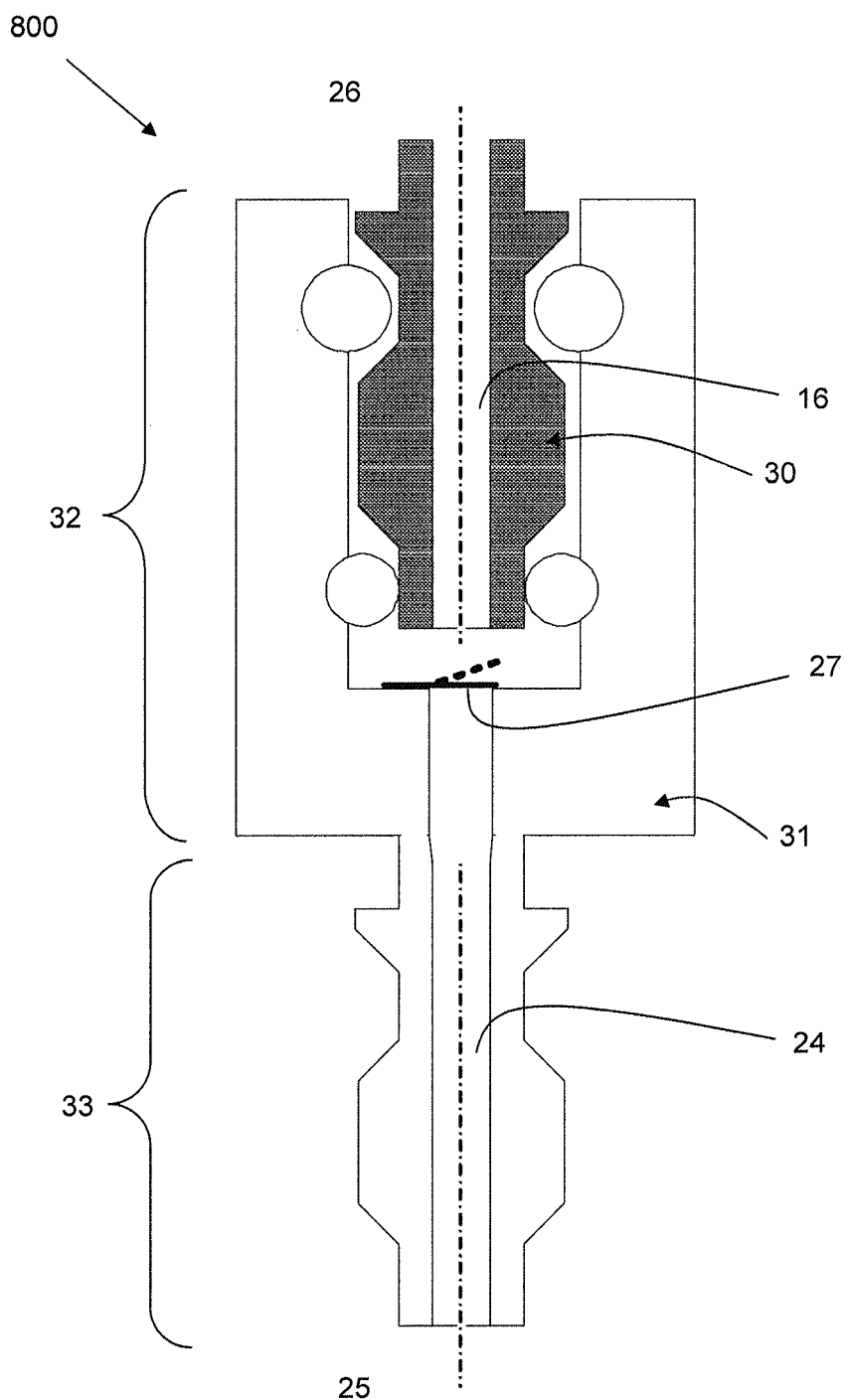
FIG. 8 shows a schematic of a sixth embodiment of the invention in a sectional view.
Figure 9:
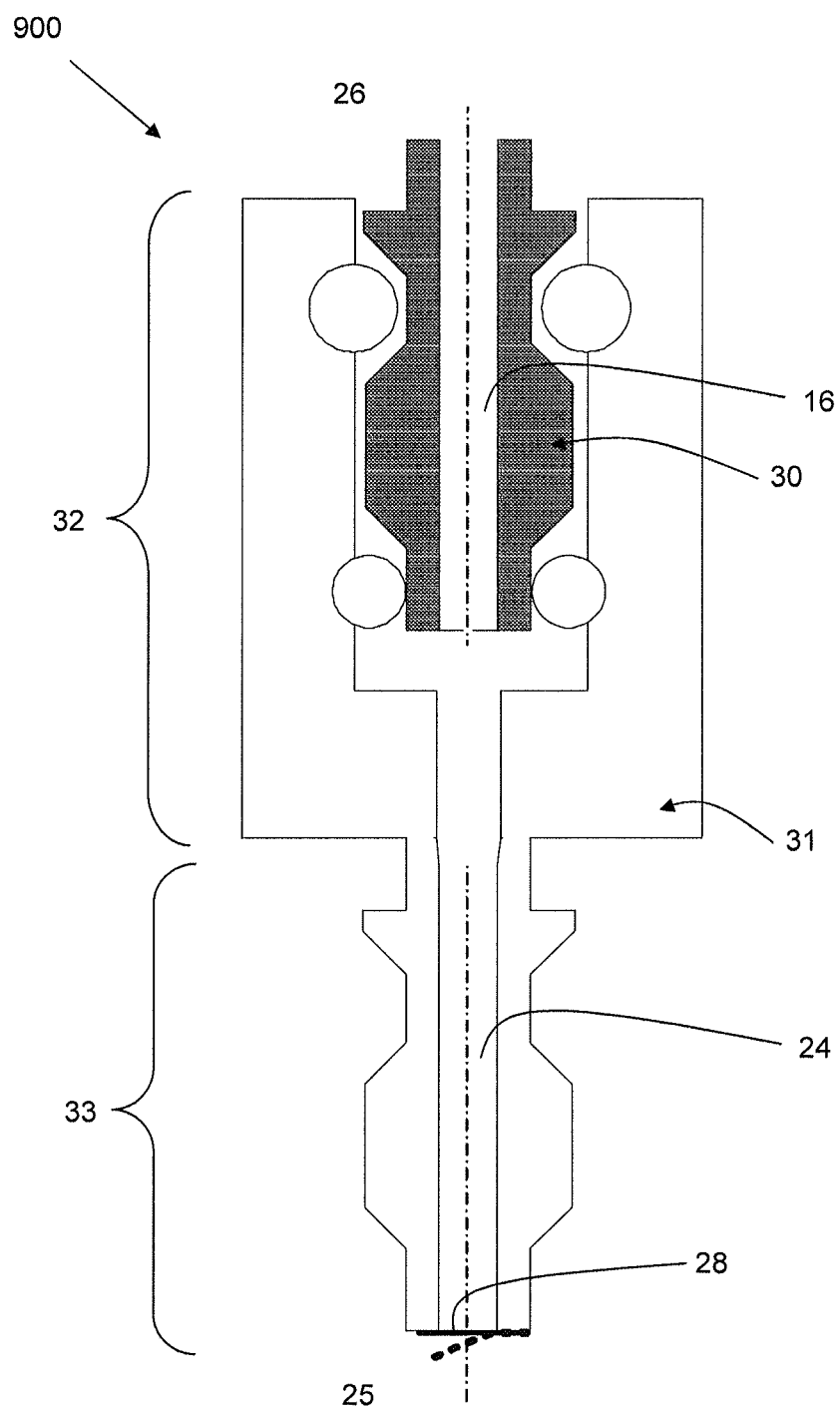
FIG. 9 shows a schematic of a seventh embodiment of the invention in a sectional view.

Other than shown in the afore-mentioned embodiments of FIGS. 6 and 7, at the connector element 31 of the embodiments of the FIGS. 8 and 9, similarly to the embodiment of FIGS. 3 and 4, a check valve 27 or, respectively, 28 is arranged for blocking and releasing the flow channel 24. The corresponding remarks concerning FIGS. 3 and 4 are referred to. In the embodiment of FIG. 8 the check valve 27 is arranged at the female coupling portion 32 on the side of the connector element 31 facing the connector element 30 and at an appropriate pressure opens to the inside, i.e. toward the connector element 30. In the embodiment of FIG. 9 the check valve 28 is arranged at the male coupling portion 33 on the fluid line side 25 and opens at an appropriate pressure to the outside, i.e. toward one of the lines 3, 9, 10, 12.

The substantial advantage of the embodiments shown in FIGS. 8 and 9 can be perceived in the fact that the connector element 31 virtually acts as a kind of adapter and thus enables that neither the connection 30 at the dialyzer nor the connector element 23 at the line 3, 9, 10, 12 to be connected has to be modified or adapted in any way. Thus any presently available system may be refitted with the connector 800 and, respectively, 900. The connector element 31 on the one hand is disposed at the dialyzer connection 30 and closes the same. When connecting the connector element 31 to a connector element 23 of the line 3, 9, 10, 12 and subsequently pumping fluid through the lines, the fluid communication between the dialyzer 5 and the line 3, 9, 10, 12 is opened or established, as the pump pressure opens the check valve(s) 27, 28, 29.

Figure 10:
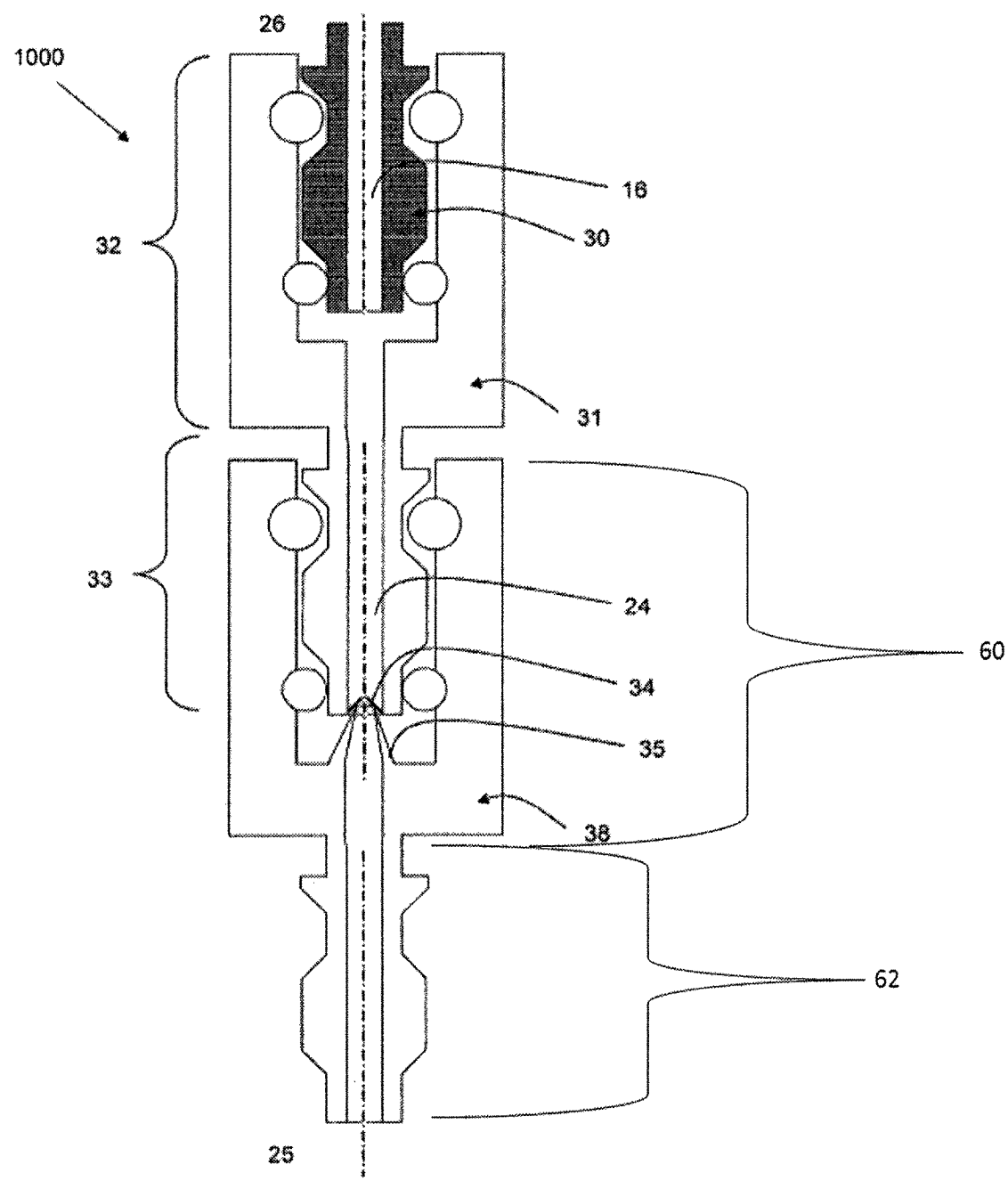
FIG. 10 shows a schematic of an eighth embodiment of the invention in a sectional view.

In the embodiment of FIG. 10 a shut-of device 70 in the form of a mechanically operable or moveable closing element/port 34 is arranged in the connector element 31 of the connector unit 1000 in the area of the end thereof facing the lines 3, 9, 10, 12 similarly to the embodiment of FIG. 6. The respective explanations concerning the embodiment of FIG. 6 are referred to. On the line side a further connector element 38 is coupled to the connector element 31, equally as a Hansen type connection, which includes, as also the connector element 31, a female coupling portion 60 and a male coupling portion 62.

Figure 11:
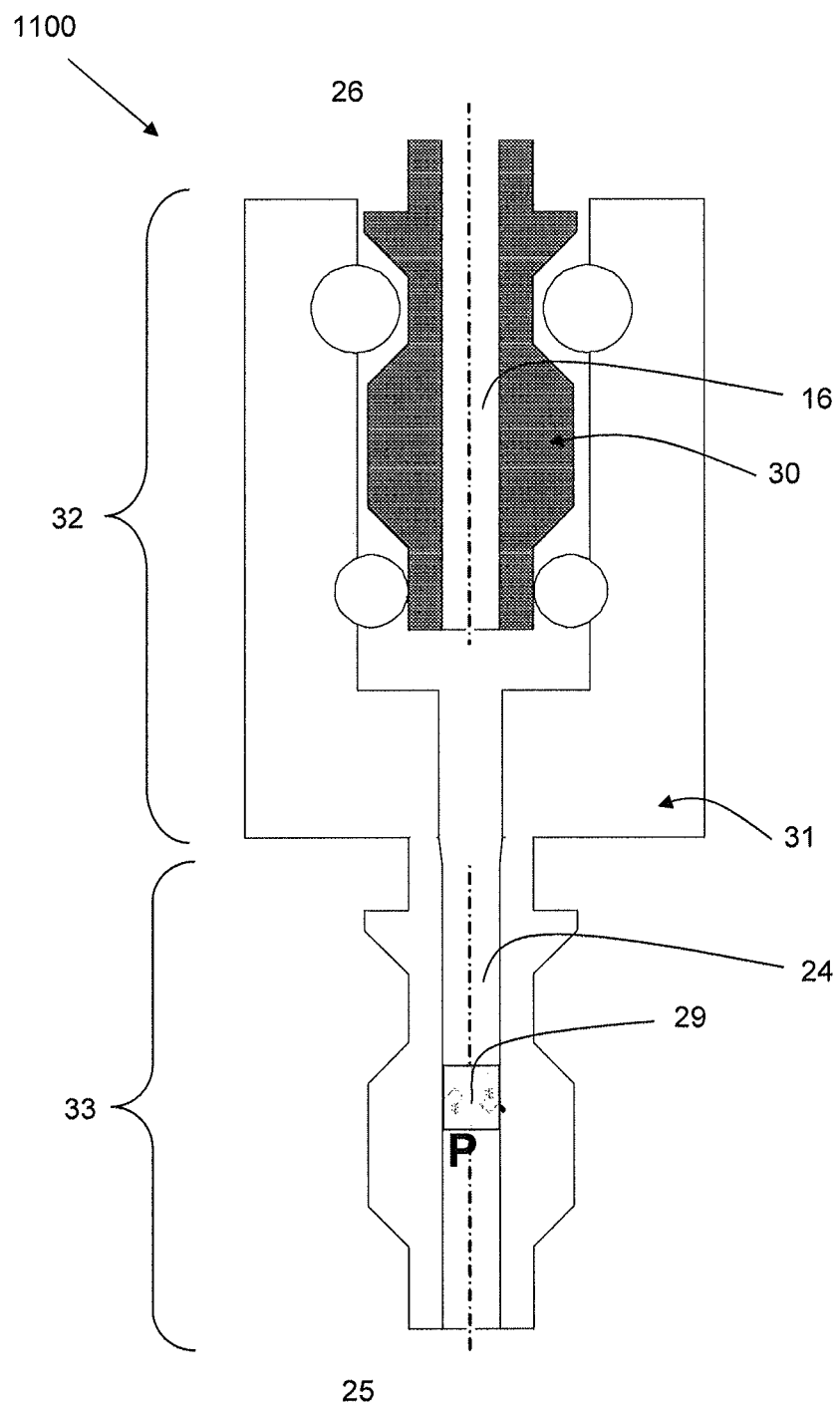
FIG. 11 shows a schematic of a ninth embodiment of the invention in a sectional view.

In the embodiment of FIG. 11 a valve system 29, which operates in a pressure-dependent and direction-independent way, is arranged in the connector element 31 of the connector unit 110 in the area of its end 25 facing the lines 3, 9, 10, 12, similarly to the embodiment of FIG. 6. The respective explanations concerning the embodiment of FIG. 6 are referred to.

Figure 12:
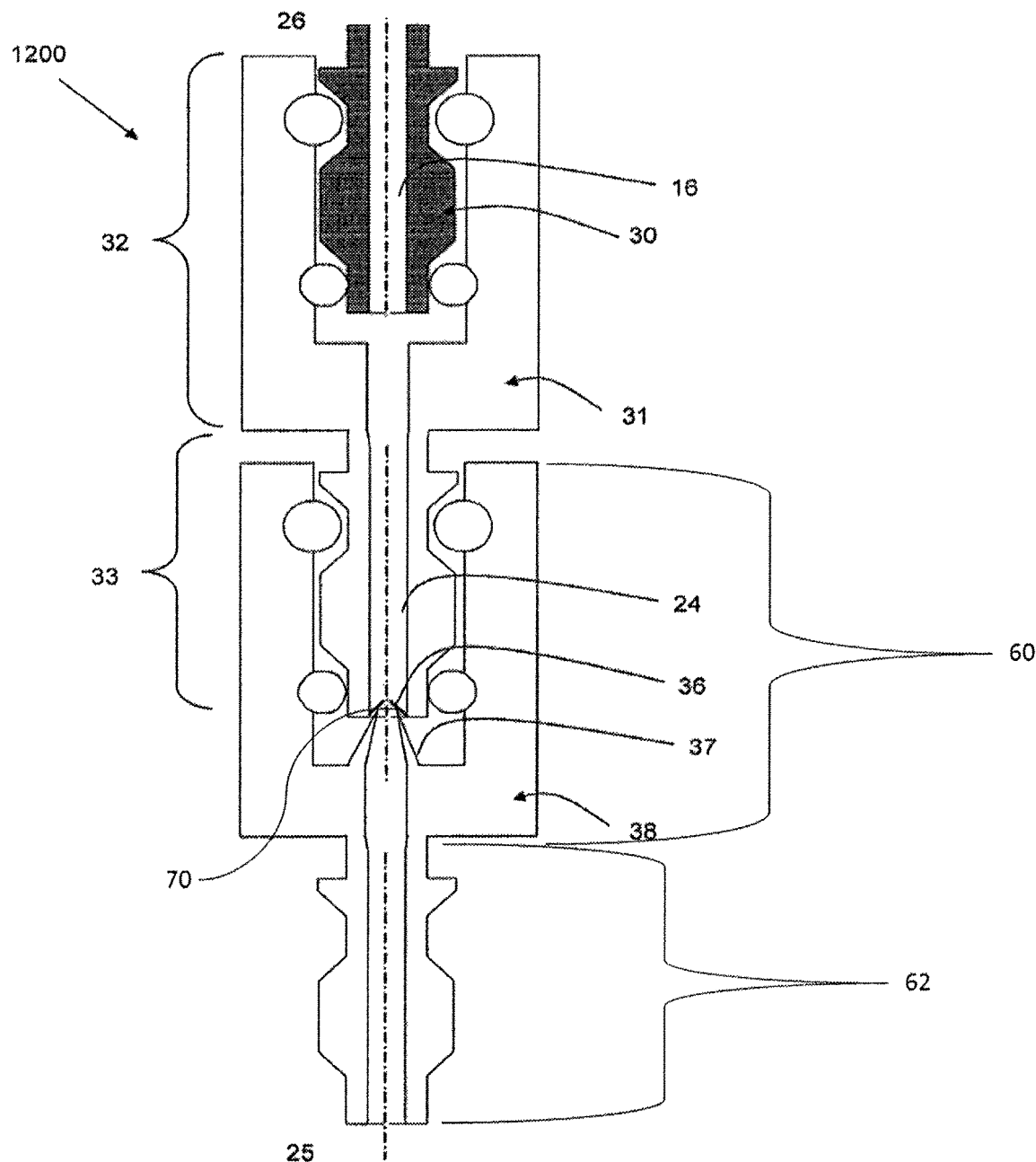
FIG. 12 shows a schematic of a tenth embodiment of the invention in a sectional view.

In the embodiment of FIG. 12 a shut-off device 70 in the form of a hydrophobic membrane 36 is arranged in the connector element 31 of the connector unit 1200 in the area of its end 25 facing the lines 3, 9, 10, 12. The respective explanations concerning the embodiment of FIG. 7 are referred to. On the line side another connector element 38 is coupled to the connector element 31, equally as a Hansen type connection, which includes a female coupling portion 60 and a male coupling portion 62 just as the connector element 31.

The substantial advantage of the embodiments shown in FIGS. 10 and 12 has to be perceived in the fact that the two connector elements 31 and 38 virtually act as a kind of adapter or adapter set and in this way enable that neither the port 30 at the dialyzer nor the connector element 23 at the line 3, 9, 10, 12 to be connected has to be modified or adapted in any way. Thus any presently available system can be refitted with the connector 1000 and, respectively, 1200 and with the connector elements 31 and 38. The connector element 31 is arranged at the dialyzer port 30 and closes the same and the connector element 38 is arranged at the line 3, 9, 10, 12, and more exactly at the connector element 23. When connecting the two connector elements the fluid communication between the dialyzer 5 and the line 3, 9, 10, 12 is opened or established, as during connection the connector element 38 (necessarily) opens the shut-off device 70 in the form of the mechanically operable or movable closing element/port 34 or, respectively, the hydrophobic membrane 36.

The invention claimed is:

1. A connector for connecting a dialyzer to a fluid-carrying line, the dialyzer including a port having a coupling portion in the form of a first male connector adaptor, wherein the connector includes:
   a first connector element configured for connection to the fluid-carrying line, wherein the first connector element has:
      a female connector adapter on an end of the first connector element, and
      a second male connector adapter disposed on an opposite end of the first connector element, the second male connector adapter configured to connect to the fluid-carrying line;
   a second connector element connecting the first connector element with the coupling portion of the port of the dialyzer in a fluid-tight manner, wherein the second connector element has:
      a third male connector adapter on an end of the second connector element, the third male connector adapter configured to couple with the female connector adapter of the first connector element, and
      a second female connector adapter disposed on an opposite end of the second connector element, the second female connector adapter configured to couple with the first male connector adapter of the coupling portion;
   a flow channel extending through the first connector element, the second connector element, and the coupling portion; and
   a shut-off device integrated in the flow channel of the connector configured to shut off a flow cross-section of the flow channel when at least one of a predetermined pressure is below a predetermined limit value or no fluid communication is provided between the dialyzer and the fluid carrying line.

2. The connector of claim 1, wherein the first male connector adapter of the coupling portion is a male Hansen connector adapter and the second female connector adapter of the second connector element is a female Hansen connector adapter.

3. The connector of claim 1, wherein the shut-off device is configured to open independent of flow direction through the flow channel.

4. The connector of claim 3, wherein the shut-off device includes a bidirectional check valve.

5. The connector of claim 1, wherein the shut-off device interacts with an actuator provided by the first connector element such that the shut-off device opens when the female connector adapter of the first connector element is connected to the third male connector adapter of the second connector element.

6. The connector of claim 1, wherein the shut-off device includes a membrane that shuts off the flow cross-section and interacts with a projection element provided at the first connector element such that the membrane is pierced when the female connector adapter of the first connector element is connected to the third male connector adapter of the second connector element.

7. The connector of claim 6, wherein the membrane is a hydrophobic membrane and the projection element is a puncturing element.

8. The connector of claim 1, wherein the second connector element is configured to provide a releasable and fluid-tight connection to the dialyzer.

9. The connector of claim 8, wherein the second connector element is a quick-release connector element.

10. The connector of claim 1, wherein the second female connector adapter of the second connector element is a female Hansen connector adapter for coupling to a corresponding male Hansen connector element formed as the first male connector adapter of the coupling portion; and the second male connector adapter of the first connector element is a male Hansen connector element for coupling to a corresponding female Hansen connector adapter formed at the fluid-carrying line, the shut-off device being provided in the second connector element.

11. A dialyzer for an extracorporeal blood treatment comprising:
    a blood supply line port;
    a blood drain line port;
    a dialysis fluid supply line port;
    a dialysis fluid drain line port; and
    a connector of claim 1 formed integrally with the dialyzer or detachably arranged on at least one of the blood supply line port, the blood drain line port, the dialysis fluid supply line port, or the dialysis fluid drain line port.

12. A method of flushing a filter element of a dialyzer for extracorporeal blood treatment, the dialyzer comprising a blood supply line port, a blood drain line port, a dialysis fluid supply line port, and a dialysis fluid drain line port, wherein a blood supply line connector is arranged on the blood supply line port and a blood drain line connector is arranged on the blood drain line port, the blood supply line connector and the blood drain line connector each according to the connector of claim 1, the method comprising:
    coupling a washing fluid supply line to the blood supply line connector arranged at the blood supply line port; and
    coupling a washing fluid drain line to the blood drain line connector arranged at the blood drain line port.

13. The method of claim 12, wherein a dialysis fluid supply line connector is arranged on the dialysis fluid supply line port and a dialysis fluid drain line connector is arranged on the dialysis fluid drain line port, the dialysis fluid supply line connector and the dialysis fluid drain line connector each according to the connector.

* * * * *